United States Patent [19]

Fukunaga

[11] Patent Number: 5,525,340
[45] Date of Patent: Jun. 11, 1996

[54] FOOD COMPOSITION CONTAINING ANTIMICROBIAL PLANT DISTILLATE

[75] Inventor: Toshikazu Fukunaga, Hyogo, Japan

[73] Assignees: Shiraimatsu Shinyaku Kabushiki Kaisha, Minakuchi-cho; Itochu Fine Chemical Corporation, Tokyo, both of Japan

[21] Appl. No.: 189,143

[22] Filed: Jan. 31, 1994

[30] Foreign Application Priority Data

Feb. 2, 1993 [JP] Japan .................................. 5-039517

[51] Int. Cl.$^6$ ..................................................... A61K 35/78
[52] U.S. Cl. .................................. 424/195.100; 426/615; 514/783
[58] Field of Search ......................... 424/195.1; 426/615; 514/783

[56] References Cited

U.S. PATENT DOCUMENTS 4,707,263 11/1987 Nishimori et al. ..................... 210/484

FOREIGN PATENT DOCUMENTS

| 60-32705 | 2/1985 | Japan . |
| 63290825 | 11/1988 | Japan . |
| 02189804 | 7/1990 | Japan . |
| 04200363 | 7/1992 | Japan . |
| 04248978 | 9/1992 | Japan . |
| 05007453 | 1/1993 | Japan . |
| 1148617 | 4/1985 | U.S.S.R. . |

OTHER PUBLICATIONS

Translation of Claim 2 of Japanese Application referenced above.
Spraul et al. *Chem. Mikrobiol. Technol. Lebensm.*, vol. 13(5/6), pp. 179–182, (1991).
Ivanisenko et al. *Fiziol. Akt. Veshchestva*, vol. 19, pp. 75–77, (1987).
Li et al. *Fujian Shifan Daxue Xuebao, Ziran Kexueban*, vol. 6(2), pp. 74–82, (1990).
Nishina *Gekkan Fudo Kemikaru*, vol. 7(5), pp. 36–39, (1990).
Yen et al. *J. chin. Agric. Chem. Soc.*, vol. 29(2), pp. 119–134, (1991).
Sofos et al. *Dev. Food. Sci.*, vol. 17, pp. 453–472, (1988).
Getmanskii et al. *Maslo–Zhir. Prom.*, vol. 35(5),pp. 25–28, (1969).
Toriqoe, et al. Chem. Abs. 78:96259a, 1973.

*Primary Examiner*—Douglas W. Robinson
*Assistant Examiner*—Howard C. Lee
*Attorney, Agent, or Firm*—Armstrong, Westerman, Hattori, McLeland & Naughton

[57] ABSTRACT

The present invention relates to an antimicrobial composition of matter comprising a dry distillate of at least one plant other than beefsteak plant, bamboo, ginger, mugwort, and garlic. The plant may be selected from, for example, *Sasa veitchii, Aspalathus linearis* (rooibos tea) Guinea pepper, sesame, and parsley. In addition, the present invention relates to shaped articles containing or carrying the composition of matter as well as a method of producing the composition of matter.

1 Claim, No Drawings

FOOD COMPOSITION CONTAINING ANTIMICROBIAL PLANT DISTILLATE

FIELD OF THE INVENTION

This invention relates to an antimicrobial composition of matter derived from a certain cohort of plants and having remarkably high antimicrobial activity, shaped antimicrobial articles either containing or carrying said antimicrobial composition of matter and a method of producing said antimicrobial composition of matter.

BACKGROUND OF THE INVENTION

It is known that aqueous and organic extracts of certain plants including ginger, bamboo grass, mugwort, etc. contain antimicrobially active principles. By way of illustration, Japanese Patent Kokai No. 32705/1985 discloses an antimicrobial composition containing a ginger rhizome extract as an active ingredient.

Derived from naturally-occurring sources, namely plants, such antimicrobial substances are safe and expected to find application in the field of food and cosmetic additive ingredients, among others.

Moreover, though unrelated to antimicrobial use, Japanese Patent Publication No. 8694/1986 describes a deodorant composition containing a dry distillate of tea leaf boiling between 180° and 200° C. at 20 mmHg, for instance.

While antimicrobial agents extracted from plants are generally more desirable than synthetic preservatives and synthetic antimicrobial agents as far as safety is concerned, they are usually less active than the synthetic substances. Moreover, because of the characteristic odor, taste and color which trace back to the source plant, a natural substance is often considered unacceptable for food or cosmetic use. Furthermore, the extraction process required is not only time-consuming but entails a complicated after-treatment.

The inventor of this invention having done an extensive exploration into antimicrobial substances occurring in plants arrived at the assumption that antimicrobial substances in situ, namely in plants, are mostly in a masked state as its functional groups intrinsic to antimicrobial activity are bound to each other to form a condensate or polymer and such condensed or polymerized substance, if extracted, would not fully deploy its antimicrobial potential. Starting from that assumption, the inventor did further research and developed this invention.

The object of this invention is to provide an antimicrobial composition of matter having high antimicrobial activity and substantially free of the characteristic odor, taste and color of the source plant.

Another object is to provide a shaped antimicrobial article either containing or carrying said substance.

It is a further object of this invention to provide a method of producing said antimicrobial composition of matter.

SUMMARY OF THE INVENTION

The antimicrobial composition of matter according to this invention is a dry distillate of at least one plant other than beefsteak plant, bamboo, ginger, mugwort and garlic.

The shaped antimicrobial article of this invention is an article either containing or carrying the above antimicrobial composition of matter within or on the surface thereof.

The method of producing an antimicrobial composition of matter according to this invention comprises subjecting the whole, rhizome, foliage or other part of a plant other than beefsteak plant, bamboo, ginger, mugwort and garlic to dry distillation under reduced pressure at high temperature.

In accordance with this invention, one or more plants other than beefsteak plant, bamboo, ginger, mugwort and garlic are used as the source plants. Since the use of beefsteak plant, bamboo, ginger, mugwort and/or garlic gives antimicrobial compositions of matter having particularly high activity, the invention involving the use of these specific plants is described in a copending application and is, therefore, excluded from the instant application.

The plants to which this invention can be applied cover a very broad range of vegetations inclusive of crude and Kampo (Chinese medicine) drugs, edible plants, spices, trees and shrubs, algae, mushrooms and so on. Thus, the following can be mentioned by way of example.

Madder, *Mallotus japonicus*, thistle, aloe, hydrangea, apricot, morning glory, *Rehmannia glutinosa*, akebi, azuki, barrenwort, yew tree, fig tree, *Achyranthes bidentata*, Japanese knotweed, *Acanthopanax sieboldianus*, self-heal, turmeric, *Aralia chinensis, Quercus salicina*, melon, ume tree, common fennel, Cassia Tora, Corydalis, Japanese pagoda tree, goldthread, *Sinomenium acutum*, plantain, Saint-John's-wort, *Phodea japonica, Patrinia scabiosaefolia*, tiger lily, elecampane, *Boschniakia rossica*, valerian, camomile, persimmon tree, *Cassia minosoides, Uncaria rynchophylla*, jack-in-the-culprit, licorice, Japanese nutmeg, *Artemisia capillaris*, spikenard, zedoary, mustard plant, *Trichosanthes kirilowii*, Chinese bellflower, Amur cork, Chinese matrimony vine, arrowroot, Cape jasmine, *Sophora flavescens*, walnut tree, mulberry tree, *Rhamnus japonica, Sasa veitchii*, chlorella, cranesbill, keigai, unpolished rice, candock, *Evodia rutaecarpa*, cucumber tree, burdock, sesame, comfrey, *Scutellaria baicalensis*, sea tangle, cherry tree, pomegranate, *Alisma plantago-aquatica*, kadsura japonica, saffron, hawthorn, *Cimicifuga simplex*, black cohosh, smilax, *Cornus officinalis*, Japanese pepper tree, *Hedychium spicatum, Zizyphus vulgaris*, shikusha, herbaceous peony, *Ophiopogon japonicus*, rhododendron, jashoshi, *Angelica pubescens*, tear grass, hemp palm, shiitake, Japanese honeysucle, field horsetail, Japanese green gentian, *Cnidium officinale*, senna, Japanese bead tree, herb bennet, dandelion, Japanese angelica tree, rhubarb, *Illicium verum*, bitter orange, *Panax repens*, datura, *Polyporus umbellatus*, ginseng, cogongrass, tea plant, *Galeola septentrionalis, Arisaema serratum*, Guinea pepper, *Angelica acutiloba, Eucommia ulmoides, Benincasa hispida*, Indian corn, *Houttuynia cordata*, hibiscus jujube tree, nandin, eggplant, fringed pink, *Picrasma quassioides*, elder tree, cinnamon tree, scallion, sumac, dodder, silk tree, Welsh onion, wild rose, polypody, angelica, Crickweed, adlay, *Glehnia littoralis*, Japanese mint, senna, Japanese banana plant, aspidistra, cottonweed, lotus, *Scopolia japonica*, nut grass, black bamboo, cluster-amaryllis, *Rabdosia japonica*, water caltrop, loquat, betal palm tree, club moss, *Hizikia fusiforme*, butterbur, *Amur adonis*, Japanese wistaria, thoroughwort, dishcloth gourd, tree peony, Japanese bladder cherry, balsam, *Magnolia hypoleuca*, silvervine, mahuang, Corsican weed, mandarin orange, *Bupleurum scorzoneraefolium, Euchresta japonica*, gromwell, Phoeo, rose of Sharon, peach tree, dyer's grape, yam, myrica, cornflower, creeping saxifrage, citron, *Angelica dahurica*, gentian, weeping golden bell, Japanese horseradish, wakame seaweed and so on.

The plant, either the whole or a part thereof, is crushed and dried, if necessary, and subjected to dry source material.

The plant, either the whole or a part thereof, is crushed and dried, if necessary, and subjected to dry distillation to provide the objective antimicrobial composition of matter. This dry distillation is carried out at high temperature and under reduced pressure. The typical conditions of dry distillation are 120°–250° C., preferably 130°–220° C. and more desirably 140°–210° C., and not more than 100 mmHg, preferably ≦60 mmHg, more desirably 10–50 mmHg, and especially 15–40 mmHg. If the temperature is too low, the necessary pyrolysis does not proceed to a satisfactory extent, while too high a distillation temperature results in excessive carbonization and a reduced yield. On the other hand, if the degree of vacuum is insufficient, the yield of the desired distillate will be decreased. The initial fraction of the distillate may be cut off.

The dry distillate thus obtained is usually a viscous fluid but for the ease of handling, it can be diluted with water, ethanol, propylene glycol or the like. The dry distillate may also be further purified.

The activity of the antimicrobial composition of matter obtained by the above procedure is specific to the source plant. Therefore, to obtain an extended antimicrobial spectrum, it is preferable that two or more different plants be subjected together to dry distillation or dry distillates from two or more different plants be used in admixture. Moreover, the dry distillate from any of said plants may be used in combination with other antimicrobial substances.

The antimicrobial composition of matter obtainable by the above dry distillation procedure is of value as a food or cosmetic supplement or an additive for quasi-drug use, for instance. Thus, the antimicrobial composition of matter according to this invention can be used as an antistaling agent to be incorporated in, or supported on, a sheet or tray for holding food or incorporated in, or supported on, a wrapping paper for wrapping food, an antiseptic to be added to water tanks for aquarium fish, or a cut-flower antiwithering agent. Thus, the term "antimicrobial composition of matter" is used herein to mean any antimicrobially active material whether it can be more properly termed an antibacterial agent, antifungal agent, bacteriostatic agent, antiseptic, preservative, anti-withering agent or the like.

It is suspected that generally the antimicrobial substances in plants are partly present in the free form but mostly in the form of complexes formed as their functional groups pertinent to antimicrobial activity are bound to each other by condensation or polymerization. Therefore, mere extraction of them with water or an organic solvent leaves such complexes intact so that the antimicrobially active functional groups remain masked. Therefore, extracts of plants are lean in the free form of active substances and accordingly show only moderate activity.

In the method of this invention, however, the plant tissue is exposed to the high-temperature and vacuum conditions of dry distillation, with the result that the above-mentioned complexes are thermally decomposed to unmask the antimicrobially active functional groups and, hence, the distillates are rich in the active substances. Thus, the dry distillation according to this invention not only serves to thermally decompose said complexes but also enables fractional recovery of the antimicrobial composition of matter.

EXAMPLES

The following examples are intended to describe this invention in further detail.

Examples 1–2

*Sasa veitchii* were dried and antimicrobial principles were separated from the materials by the following three methods.

(1) A dry distillation equipment was charged with 200 g of previously dried *Sasa veitchii* and the load was dry-distilled at a temperature of about 200° C. and a reduced pressure of about 35 mmHg. The distillate was recovered in 1500 ml of ethanol.

(2) Twenty (20) grams of previously dried *Sasa veitchii* was extracted with 150 g of boiling water.

(3) Twenty (20) grams of previously dried *Sasa veitchii* was extracted with 150 g of hot ethanol.

Compared with the samples obtained by methods (2) and (3), the sample obtained by method (1) was remarkably pale in color and suppressed in odor.

Using the above three samples (1), (2) and (3), antimicrobial activity assays were carried out by the following two methods A and B.

Method A

Culture dishes, 90 mm in diameter, were each filled with 1 ml of the sample and 10 ml of sterilized agar medium, and after mixing, the agar was allowed to solidify. The resulting media were inoculated with 0.5 ml portions of *Aspergillus niger*, *Escherichia coli* or *Staphylococcus aureus* suspensions, respectively, and incubated at 35° C. for 48 hours. Then, the growth of each microorganism was investigated. As to the bacteria, a loopful of the medium was sampled after incubation and inoculated onto an agar slant for the verification of growth. The media used was GP agar for the fungus and SCD medium for *E. Coli* and *Sta. aureus*.

Method B

Culture dishes, 90 mm in diameter, were each filled with 10 ml of sterilized agar medium and the agar was allowed to cool and solidify. The resulting media were inoculated with 0.5 ml portions of *Asp. niger*, *E. coli* and *Sta. aureus* suspensions. Separately, 0.1 ml of each sample was dripped on a paper disk, 10 mm in diameter, and allowed to stand at room temperature for 1 hour to dry. This drying procedure of short duration was intended to prevent diffusion of the sample. The dried disk was then placed on the inoculated medium and incubated at 35° C. for 48 hours to check for the growth of the microorganism. The medium used was GP agar for the fungus and SCD medium for *E. coli* and *Sta. aureus*.

In method A, the results were evaluated according to the following criteria.

Fungus
−: Growth is found in entire area
+: No growth in less than 50% of area
++: No growth in 50% or more of area
+++: No growth at all Bacteria
−: Colonies are found in entire area
+: No colonies in less than 50% of area
++: No colonies in 50% or more of area
+++: No colonies at all The growth on the slant medium was evaluated on the two-stage scale of o (no growth) and x (growth).

In method B, the following evaluation criteria were used.

Fungus
−: Growth is found on entire disk
+: No growth on part of disk
++: No growth on disk
+++: A zone of inhibition is found Bacteria
−: No zone of inhibition around disk
±: A zone of inhibition within 1 mm from periphery of disk
+: A zone of inhibition within 5 mm from periphery of disk ++: A zone of inhibition beyond 5 mm from periphery of disk The data obtained by method A are shown in Table 1 and those obtained by method B in Table 2. The results of blank tests using ethanol alone are also shown as controls in Tables 1 and 2.

TABLE 1

| Plant | | Asp. niger | E. Coli | Sta. aureus |
|---|---|---|---|---|
| Sasa veitchii | Dry distillate | +++ | ++/x | +++/o |
| | Aqueous extract | − | −/x | +/x |
| | Ethanol extract | + | −/x | −/x |
| Control | (Ethanol) | + or − | −/x | −/x |

TABLE 2

| Plant | | Asp. niger | E. Coli | Sta. aureus |
|---|---|---|---|---|
| Sasa veitchii | Dry distillate | ± | ± | + |
| | Aqueous extract | ± | − | − |
| | Ethanol extract | − | − | − |
| Control | (Ethanol) | − | − | − |

Examples 2–5

Using *Aspalathus linearis* (rooibos tea) (Example 2), Guinea pepper (Example 3), sesame (Example 4) and parsley (Example 5) instead of *Sasa veitchii*, the dry distillation, aqueous extraction and ethanol extraction procedures of Example 1 were otherwise repeated to provide the respective samples.

The antimicrobial activity of each sample obtained above was assayed as in Example 1. The data obtained by method A are shown in Table 3 and those obtained by method B in Table 4. The results of blank tests using ethanol alone are also shown as controls in Tables 3 and 4. Compared with the aqueous and ethanol extracts, the dry distillates were by far pale in color and suppressed in odor.

TABLE 3

| Plant | | Asp. niger | E. Coli | Sta. aureus |
|---|---|---|---|---|
| Aspalathus linearis (rooibos tea) | Dry distillate | ++ | ++/x | +++/o |
| | Aqueous extract | + | −/x | −/x |
| | Ethanol extract | + | −/x | −/x |
| Guinea pepper | Dry distillate | + | +/x | +++/o |
| | Aqueous extract | − | −/x | −/x |
| | Ethanol extract | + | −/x | −/x |
| Sesame | Dry distillate | + | +/x | −/x |
| | Aqueous extract | − | −/x | −/x |
| | Ethanol extract | − | +/x | −/x |
| Parsley | Dry distillate | ++ | −/x | +/x |
| | Aqueous extract | ++ | −/x | +/x |
| | Ethanol extract | − | +++/x | −/x |
| Control | (Ethanol) | + or − | − or +/x | −/x |

TABLE 4

| Plant | | Asp. niger | E. Coli | Sta. aureus |
|---|---|---|---|---|
| Aspalathus linearis (rooibos tea) | Dry distillate | ± | ± | +++/o |
| | Aqueous extract | − | − | − |
| | Ethanol extract | − | − | − |
| Guinea pepper | Dry distillate | ± | − | − |
| | Aqueous extract | − | − | − |
| | Ethanol extract | − | − | − |
| Sesame | Dry distillate | + | + | − |
| | Aqueous extract | ± | − | − |
| Parsley | Ethanol extract | − | − | − |
| | Dry distillate | ± | + | ± |
| | Aqueous extract | ± | − | − |
| | Ethanol extract | ± | − | − |
| Control | (Ethanol) | − or ± | − | − |

Example 6

The dry distillates, aqueous extracts and ethanol extracts of *Sasa veitchii, Aspalathus linearis* (rooibos tea), Guinea pepper, sesame and parsley used in the foregoing examples were respectively added to rice cake, bread dough, sausage and miso (bean paste) batches at the level of 1% by weight (inclusive of solvent). The respective food products were then prepared and their shelf-lives were investigated. Using the corresponding product not containing any of the additives as control, the activity of each antimicrobial additive was evaluated on the 3-grade scale of C (no change), B (effective) and A (very effective). The results are shown in Table 5.

TABLE 5

| | Rice cake | Bread | Sausage | Miso |
|---|---|---|---|---|
| *Sasa veitchii* | | | | |
| Dry distillate | A | A | B | A |
| Aqueous extract | B–C | C | C | C |
| Ethanol extract | B–C | C | B | C |
| *Aspalathus linearis* (rooibos tea) | | | | |
| Dry distillate | A–B | A–B | A | A |
| Aqueous extract | B–C | C | C | C |
| Ethanol extract | B–C | C | C | C |
| Guinea pepper | | | | |
| Dry distillate | B–C | B–C | A–B | B |
| Aqueous extract | C | C | C | C |
| Ethanol extract | B–C | B–C | C | C |
| Sesame | | | | |
| Dry distillate | B–C | B–C | C | B–C |
| Aqueous extract | B–C | C | C | C |
| Ethanol extract | C | C | B–C | C |
| Parsley | | | | |
| Dry distillate | B | B–C | B–C | B–C |
| Aqueous extract | B | B–C | C | C |
| Ethanol extract | C | C | B | B–C |

Example 7

Nonwoven fabrics were respectively impregnated with the dry distillates, aqueous extracts and ethanol extracts used in the Examples. After drying, each fabric was spread on a tray, slices of raw fish were placed on the fabric and the whole was wrapped up. With the aqueous extracts or ethanol extracts, the antistaling effects were almost negligible. In contrast, when the dry distillates of this invention were used, definite antistaling effects were obtained.

Thus, compared with the conventional aqueous and ethanol extracts of plants, the antimicrobial compositions of matter according to this invention are remarkably higher in antimicrobial activity and less pronounced in odor, taste and color.

Moreover, the method of this invention is advantageous in that since the necessary composition of matter can be obtained by mere dry distillation of the source plant, the production process is remarkably simple as compared with the conventional extraction procedure using water or an organic solvent.

What is claimed is:

1. A method of preparing a food composition comprising combining food product with an antimicrobial distillate obtained by the dry distillation at a temperature of 130° to 220° C. and at a pressure of 10 to 50 mmHg of at least one plant selected from the group consisting of *Sasa veitichii*, Guninea pepper, sesame, parsley and rooibos tea.

* * * * *